United States Patent [19]
Vogt et al.

[11] Patent Number: 6,121,487
[45] Date of Patent: Sep. 19, 2000

[54] METHOD OF PRODUCING AMINO ACIDS AND AMINO-ACID DERIVATIVES

[75] Inventors: Annegret Vogt, Morristown, N.J.; Hans-Josef Altenbach, Wuppertal, Germany; Michael Kirschbaum, Gross-Gerau, Germany; Michael-Gottfried Hahn, Cologne, Germany; Mike Siegfried Paul Matthaus; Andreas Rainer Hermann, both of Wuppertal, Germany

[73] Assignee: Degussa-Hüls Aktiengesellschaft, Germany

[21] Appl. No.: 09/361,711

[22] Filed: Jul. 28, 1999

[30] Foreign Application Priority Data

Jul. 28, 1998 [DE] Germany .................. 198 33 853

[51] Int. Cl.[7] .................................................. C07C 229/08

[52] U.S. Cl. .................... 562/575; 562/623; 560/155; 560/170; 560/173

[58] Field of Search ..................... 560/155, 173, 560/170; 562/575, 623

[56] References Cited

FOREIGN PATENT DOCUMENTS

97/10203  3/1997  WIPO .

OTHER PUBLICATIONS

Database CAPLUS on STN, Acc. No. 1988:611481, Dotani et al., [A process for the preparation of alpha–amino acid amides by hydrolysis of 4–imidazolidinones.] JP 6305 1339 A2 (abstract), Mar. 4, 1988.

*Primary Examiner*—Samuel Barts
*Assistant Examiner*—Brian J. Davis
*Attorney, Agent, or Firm*—Pillsbury Madison & Sutro LLP

[57] ABSTRACT

The present invention is relative to a chemical method of producing compounds of the general formula (I)

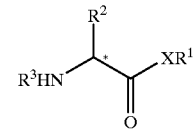

I starting from compounds of the general formula (II) and (III)

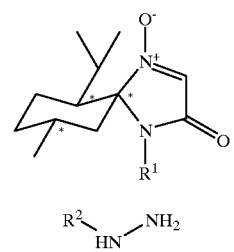

II

III under radical conditions. Products I are used as intermediates in the synthesis of bioactive substances.

29 Claims, No Drawings

METHOD OF PRODUCING AMINO ACIDS AND AMINO-ACID DERIVATIVES

CROSS-REFERENCE TO RELATED APPLICATION

This application claims priority from German Application DE 198 33 853.8, filed Jul. 28, 1998, which disclosure is incorporated herein by reference.

BACKGROUND OF THE INVENTION

1. Field of the Invention

The present invention relates to a method of producing enantiomer-enriched amino acids and amino-acid derivatives of the general formula (I) or acid addition salts thereof

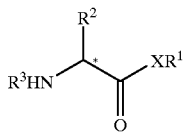

in which
* *=center of asymmetry
* X=O or NH
* $R^1$=H, ($C_1$–$C_6$) alkyl, benzyl or ($C_3$–$C_6$) alkoxycarbonylmethyl and
* $R^2$=H or ($C_1$–$C_6$) alkyl, which can be interrupted or substituted with heteroatoms such as N, P, O, S or Si, which heteroatoms can be substituted themselves singly or multiply with linear or branched ($C_1$–$C_3$) alkyl, ($C_2$–$C_6$) alkenyl, ($C_1$–$C_6$) haloalkyl, halogen, aryl, such as naphthyl or phenyl, which can be substituted singly or multiply with ($C_1$–$C_3$) alkyl, hydroxy, halogen or ($C_1$–$C_3$) alkoxy, aralkyl such as 2-naphthylmethyl or benzyl or 1,1- or 1,2-phenethyl, which for its part can be substituted singly or multiply with ($C_1$–$C_3$) alkyl, hydroxy, halogen or ($C_1$–$C_3$) alkoxy, heteroaralkyl such as N-protected 3-indolylmethyl, and
* $R^3$ signifies H or OH, from enantiomer-enriched nitrons of the general formula (II)

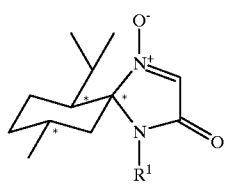

in which * and $R^1$ have the significance indicated above.

2. Background Information

Enantiomer-enriched amino acids and amino-acid derivatives are important substances in the organic synthesis of peptides and peptide-mimetic substances which are used in drugs and biologically active substances. Thus, the optically active tert.-leucine methylamide which can be produced according to the method of the invention is required in the synthesis for producing a matrix metalloproteinase inhibitor which is currently being investigated in the clinical phase for the combating of tumors (J. Med. Chem. 1998, 41, 1209–1217).

WO 97/10203 teaches a method for the addition of nucleophiles onto nitrons of the general formula (II). However, the known method is based on the use of strong bases such as alkyl metal compounds. One is therefore limited to the use of dehydrated solvents and working under inert atmosphere protective gas as well as the exclusion of any traces of water during the reaction. Such methods are difficult to carry out on an industrial scale.

A method for the addition of radical compounds to derivatives of the general formula (II) is likewise mentioned in WO 97/10203. The reaction of the derivatives (II) with a carboxylic acid in the presence of a radical starter in various solvents under the exclusion of oxygen was described there. However, under the selected conditions α-substituted nitrons are recovered after the reaction without the actually desired asymmetry on the α-C atom of the amino-acid structural element.

According to Iwamura et al. (Bull. Chem. Soc. Jpn. 1970, 43, 856–860) 1,3 addition products or nitroxides or substituted nitrons are obtained in the reaction of nitrons with radicals. In certain instances the substituted nitroxide disproportionates in nitron and hydroxylamine (Iwamura et al., Bull. Chem. Soc. Jpn. 1967, 40, 703). The products were not isolated; however, this mechanism permits a yield of only a maximum of 50% of the desired compound. 50% of the product compounds accumulate as waste, which is considered from the industrial standpoint as a not very logical product variant.

All previously described method variants for the addition of compounds to nitrons of the formulas (II) (see WO 97/10203) have the disadvantages that they supply only moderate yields, especially in the case of bulky amino acids, and in some instances require a complicated conduction of the reaction (metallo-organic reagents, exclusion of water,e purification, etc.).

SUMMARY OF THE INVENTION

It is an object of the present invention to provide a method of producing enantiomer-enriched amino acids and amino-acid derivatives under radical conditions starting with the nitrons (II) with the obtention of a stereogenic center located on the α-C atom of the amino-acid structural element.

The term "under radical conditions" denotes in the framework of the invention a reaction in which at least one of the reactants has a radical nature.

This and other problems not cited in detail but which result nevertheless from the state of the art in an obvious manner are solved by a method wherein a nitron of the general formula (II) is reacted with a hydrazine derivative of the general formula (III)

in which $R^2$ has the meaning indicated above, in a solvent in the presence of a radical starter or under electrochemical conditions to diastereomer-enriched compounds of the general formula (IV)

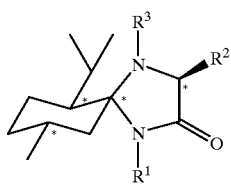

in which $R^1$ and $R^2$ have the meanings indicated above and $R^3$=OH, the product is subsequently hydrolyzed or first reduced to compounds of the general formula (IV), in which $R^1$ and $R^2$ have the meanings indicated above and $R^3$=H, and then hydrolyzed.

As a result of the fact that for the production of enantiomer-enriched amino acids and amino-acid derivatives of the general formula (I) or acid addition salts thereof

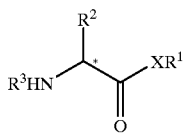

in which
* =center of asymmetry
X=O or NH
$R^1$=H, $(C_1-C_6)$ alkyl, benzyl or $(C_3-C_6)$ alkoxycarbonylmethyl and
R=H or $(C_1-C_6)$ alkyl, which can be interrupted or substituted with heteroatoms such as N, P, O, S or Si, which heteroatoms can be substituted themselves singly or multiply with $(C_1-C_3)$ alkyl, $(C_2-C_6)$ alkenyl, $(C_1-C_6)$ haloalkyl, halogen, aryl, such as naphthyl or phenyl, which can be substituted singly or multiply with $(C_1-C_3)$ alkyl, hydroxy, halogen or $(C_1-C_3)$ alkoxy, aralkyl such as 2-naphthylmethyl or benzyl or 1,1- or 1,2- phenethyl, which for its part can be substituted singly or multiply with $(C_1-C_3)$ alkyl, hydroxy, halogen or $(C_1-C_3)$ alkoxy, heteroaralkyl such as N-protected 3-indolylmethyl, and $R^3$ signifies H or OH,
diastereomer-enriched nitrons of the general formula (II)

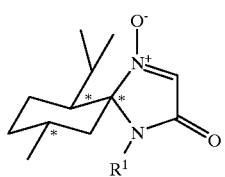

in which * and $R^1$ have the meanings indicated above are reacted in such a manner that the nitron of the general formula (II) is reacted with a hydrazine derivative of the general formula (III)

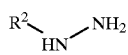

in which $R^2$ has the meaning indicated above, in a solvent in the presence of a radical starter or under electrochemical conditions to compounds of the general formula (IV)

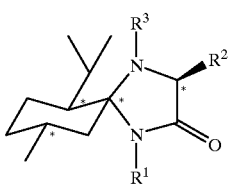

in which $R^1$ and $R^2$ have the meanings indicated above and $R^3$=OH, the product is subsequently hydrolyzed or first reduced to compounds of the general formula (IV), in which $R^1$ and $R^2$ have the meanings indicated above and $R^3$=H, and then hydrolyzed, the desired compounds are obtained in a quite extraordinarily simple and elegant manner.

The electrochemical generation of radicals from compounds of type III can take place according to methods known to the expert in the art (e.g.: F. Beck, Electroorg. [-anische] Chemie 1974, VCH-Verlag; T. Shono, Electroorganic Synthesis, 1991, Academic Press; T. Shono, Electroorganic Chemistry as a New Tool in Organic Synthesis 1984, Springer Verlag). Carbon as well as metals such as silver and platinum can be considered as electrode material. Carboxylic acid esters and alcohols, preferably acetic ester and methanol, as well as mixtures of these can be used as solvent.

The radical addition can take place at temperatures between −78° C. and 150° C., preferably −20° C. to 100° C., and especially preferably at −10° C. to 50° C. The reaction is monitored by thin-layer or gas chromatography. The end of the reaction can also be observed from the subsiding development of gas.

This reaction can be carried out in an organic solvent such as a halogenated hydrocarbon like methylene chloride, trichloromethane or dichloroethane, in esters such as acetic ester, ethers such as diethylether, MtBE, THF, dioxane, or alcohols such as methanol, ethanol, propanol, isopropanol, n-, sec-, iso-, tert.-butanol as well as in an inert, aromatic hydrocarbon such as benzene, toluene, xylene, chlorobenzene, nitrobenzene, optionally in the presence of water.

The use of a two-phase system of toluene and water is especially preferred.

In principle, all derivatives which can be considered as radical starters and are known to the expert in the art can be used for that purpose. Common radical starters are, e.g., lead dioxide, sodium- or potassium peroxodisulfate, iron(III) salts, sodium nitrite, hydrogen peroxide, sodium periodate, sodium hypochlorite, sodium perborate, sodium percarbonate or meta-chloroperbenzoic acid (see also Houben-Weyl, "Methoden der Organischen Chemie" ["Methods of Organic Chemistry"], vol. E19a, part 1, pp. 140ff, as well as part 2, e.g., pp. 1201ff; vol. E16a, pp. 805ff; vol. X/2, pp. 68ff, E. J. Corey; A. W. Gross, J. Org. Chem. 1985, 50 5391).

The use of oxidizing agents such as sodium- or potassium peroxodisulfate, sodium percarbonate or sodium perborate is especially preferred.

The reduction of the hydroxylamines (IV) with $R^3$=OH to the corresponding amines with $R^3$=H can take place in a known manner (Houben-Weyl, vol. 11/1, pp. 341ff). Organic acids such as, for example, acetic acids, inorganic acids such as, for example, HCl, or organic solvents such as acetonitrile, alcohols, ethers, esters, hydrocarbons, $CS_2$ can be used as solvents as a function of the reduction method used. The reaction temperature is between −20° C. and +120° C., preferably between +20° C. and +60° C. The addition of the reducing agent can take place in hyperstoichiometric amounts (1 equivalent relative to IV) and in catalytic amounts.

Commercial catalysts such as, for example, Pd/C, Rh/Al$_2$O$_3$, Pt/C, Raney nickel, Raney cobalt, copper chromite, platinum oxide, palladium hydroxide can be used for the catalytic reduction. The hydrogenolytic reduction can take place at normal pressure or pressures up to 50 atm.

The reduction preferably takes place in the presence of CS$_2$, zinc or hydrogenolytically with Pd/C, Pt/C or Ra Ni. The catalytic hydrogenation of IV with R$^3$=OH with Pd/C is especially preferred, which can optionally be carried out in hydrochloric-acid solution at normal pressure and room temperature, if necessary under the addition of ethanol.

The hydrolysis of compounds of the general formula (IV) with R$^3$=H to the L- and/or D-amine-acid derivatives with R$^3$=H can take place analogously to WO 97/10203 in an acidic reaction environment such as, for example, in the presence of an inorganic acid such as HCl, HBr or H$_2$SO$_4$, and/or an acidic cation exchanger and/or an organic acid such as para-TsOH, camphor sulfonic acid, bromocamphor sulfonic acid or acetic acid, and/or an organic solvent such as toluene or methanol. The reaction can take place at temperatures between 0° C. and 140° C. at normal pressure or in an autoclave. The workup and isolation take place in a customary manner and analogously to D. Seebach, R. Fitzi, Tetrahedron 44 (1988) 5277. The variant in which the hydrolysis is carried out in aqueous hydrochloric acid is quite especially preferred.

Either optically active α-amino-acid amides or the corresponding α-amino acids can be obtained by suitably carrying out the reaction as a function of temperature and concentration of acid (cf. D. Seebach, E. Juaristi, D. Müller, Ch. Schickli and Th. Weber, Helv. Chim. Acta, 70 (1987), 237).

The hydrolysis of the compounds of general formula IV with R$^3$=OH to the L- and/or D-hydroxylamino-acid derivatives of formula I with R$^3$=OH and X=NH takes place analogously to WO 97/10203 but can be carried out much more simply in a reaction step with an alcoholic solution of a mineral acid, especially preferably with HCl in ethanol under mild conditions, especially preferably at room temperature.

The compounds of general formula I can also accumulate, depending on the conditions of hydrolysis selected, in the form of an acid addition salt such as, for example, HCl salt, HBr salt, H$_2$SO$_4$ salt, part-TsOH salt, camphor sulfonic-acid salt, bromocamphor sulfonic-acid salt or acetic-acid salt.

The compounds of general formula (IV), in which R$^1$ and R$^2$ have the meanings indicated above and R$^3$=OH, can be optionally eliminated to compounds of the general formula V

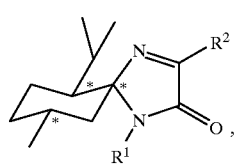

in which R$^1$ and R$^2$ have the meanings indicated above, and subsequently reduced and hydrolyzed to the compounds of general formula (I) with R$^3$=H.

The dehydration of compounds IV can take place in a known manner (Houben-Weyl, "Methoden der Organischen Chemie", vol. 10/1, p. 1247, vol. E16a, p. 211ff). Thus, for example, the hydroxylamine compound of type IV is agitated in an organic solvent such as methylene chloride, pyridine, or ether in the presence of a dehydrating agent such as N,N'-carbonyldiimidazole, DCC or P$_2$O$_5$ under the exclusion of air (e.g., N$_2$ atmosphere or argon atmosphere) at temperatures between 0° C. and 120° C., preferably between 20° C. and 30° C. and worked up after the end of the reaction.

The elimination products V can then be converted as mentioned under reducing conditions and inversion of configuration into the optical antipodes of the original type IV with R$^3$=H. The reduction can be carried out analogously to the already described reduction of compounds of type IV with R$^3$=OH to IV with R$^3$=H. The catalytic hydrogenation with Pd(OH)$_2$/C in ethanol at 25° C. and normal pressure is preferred (cf. also B. Trost, I. Fleming, Compr. Org. Syn., vol. 8, "Reductions", Pergamon Press, Oxford 1991).

The following hydrolysis of the optical antipodes of IV with R$^3$=H to compounds of type I with R$^3$=H takes place in analogy with what was described above.

In addition, it is possible, as described in WO 97/10203, to oxidize the compounds of type IV

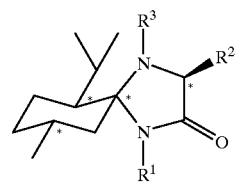

R$^3$=OH to nitrons again and to make them accessible again to a further reaction with nucleophiles. In this manner, optically active α,α-disubstituted amino-acid derivatives of general formula IV are obtained in a further reaction step.

The further reactions of the α,α-dialkyl derivatives take place analogously to the steps cited above.

The production of the compound of general formula (II) is described in WO 97/10203 but can be carried out in a more advantageous manner avoiding solvents containing chlorinated hydrocarbons and avoiding halogen-containing aromatic peracids such as 3-chloroperoxobenzoic acid in alcohols using MMPP (monoperoxyphthalic-acid magnesium salt) or by means of hydrogen peroxide in the presence of catalytic amounts of methyltrioxorhenium (MeReO$_3$).

The hydrazine (III) can be produced according to the method known to the expert in the art (Houben-Weyl, vol. E16a, p. 425 ff, editor D. Klamann and X/2, p. 1ff, editor E. Müller).

The reaction of compounds of structural type II to compounds of general formula IV takes place with the addition of monosubstituted hydrazine III, e.g., in the presence of an oxidizing agent. The diastereomerically pure compounds IV accumulate after purification by crystallization, distillation or column chromatography in yields up to 96%.

For this, the compounds of structural type II are dissolved in an organic solvent, e.g., toluene, acetic ester, ether, alcohols, etc. and compounded preferably at room temperature with 3–6 equivalents of a monosubstituted hydrazine III and 3–6 equivalents of an oxidizing agent.

Alternatively, the hydrazine III can be released in situ out of the hydrazine acid compounds by a base, e.g., sodium hydroxide, potassium hydroxide or triethylamine.

After the end of the reaction, readily recognizable from the decreasing production of nitrogen, the solid residue is simply filtered off or worked up in an aqueous manner, according to the oxidizing agents used, (separation and extraction of the aqueous phase with an appropriate organic solvent and drying of the collected organic phases). The purification of the raw products takes place by recrystallization, distillation or column chromatography.

A significant advantage of the method is the fact that the initial substances (+)-menthol as well as (−)-menthol are readily available commercially at favorable and similar prices.

In comparison to the known methods, the method of the invention permits a novel conduction of the reaction which makes possible a simpler and more rapid production of the compounds of general type I. Thus, L-α-hydroxylamino-acid derivatives or L-α-amino-acid derivatives or D-α-hydroxylamino-acid derivatives or D-α-amino-acid derivatives can be obtained in a purposeful manner, depending on the initial material selected.

Starting from (−)-menthol the corresponding L-α-hydroxylamino acids/L-α-amino acids and their derivatives can be obtained in an advantageous manner and starting from the optical antipode (+)-menthol the corresponding D-α-hydroxylamino acids/D-α-amino acids and their derivatives. The characterization of the asymmetric carbons in the cyclohexane fragment of the compounds of general formulas II and IV with * is intended to make it clear that this is a stereocenter of the configuration 6S,9R or 6R,9S, according to the initial material selected—(−)-menthol or (+)-menthol. The unambiguous and absolute configuration of the other center of asymmetry in IV results from the selection of the initial materials. Thus, the center is clearly fixed on the α-C atom of the amino-acid structural element in IV by the configuration on the cyclohexane ring.

(−)-Menthol and (+)-menthol are converted thereby in a manner known in the literature (Houben-Weyl, "Methoden der Organischen Chemie", vol. 7/2a, p. 724) by oxidation into the corresponding (−)-menthone and (+)-menthone.

The radical addition to the nitron (II) suggested here makes possible, in comparison to the previously known radical addition with subsequent hydrogenation, a more efficient synthesis of, e.g., optically active tert. leucine. Along with the shortening of the reaction sequence by one reaction stage, compared with the radical addition of WO 97/10203, the reaction takes place here with significantly higher yields. Furthermore, no cooling is necessary for monitoring the reaction temperature as in the reduction of the substituted nitron (II) with lithium aluminum hydride in WO 97/10203. As a result of the broad variability of the oxidizing agent for producing the radicals, heavy metals can be eliminated in an advantageous manner in contrast to the known methods.

In comparison to the described ionic methods, the increased yields of the radical addition, especially in the case of sterically demanding groups, are noted. In the case of the tert. butyl group an increase of the yield from 40% to above 96% results, with a diastereoselectivity which is likewise equally high.

Complicated reaction techniques, such as the exclusion of water, low reaction temperatures and metallo-organic reagents which are difficult to manage, can be completely eliminated.

Instead, the reaction conditions, the solvent and the oxidizing agent used can be freely selected within broad ranges. In the case of an electrochemical oxidation of the hydrazine even the formation of salt can be minimized. All known byproducts, e.g., nitrogen, alkanes, potassium sulfate, etc. are reaction products which can be safely managed on an industrial scale.

The educts used are commercially available or can be synthesized in a simple manner.

The term "alkyl" denotes both "straight-chain" and "branched" alkyl groups. The term "straight-chain alkyl group" denotes, e.g., groups such as methyl, ethyl, n-propyl, n-butyl, n-pentyl, n-hexyl and the term "branched alkyl group" denotes groups such as, e.g., isopropyl, neopentyl or tert. butyl. The designation halogen stands for fluorine, chlorine, bromine or iodine. The term "alkoxy group" represents groups such as, e.g., methoxy, ethoxy, propoxy, butoxy, isopropoxy, isobutoxy or pentoxy along with their possible bonding isomers.

Publications and patents cited herein are hereby incorporated by reference.

DETAILED DESCRIPTION OF THE INVENTION

The following examples are intended to explain the invention:

A) Oxidation to the Compound of General Formula II Using magnesium monoperoxyphthalic Acid, MMPP (0.66 mole) of the compound of type II of WO 97/10203 is placed into a mixture of 2.50 L EtOH (industrial) and 0.50 L distilled $H_2O$ (v/v=5:1) in a receiver and slowly compounded under agitation and the continuous addition via a solid worm with 403 g (0.774 mole) magnesium monoperoxyphthalic acid hexahydrate (85%) at a temperature of 35–45° C. within 1.5 h. A transformation to the desired end product of 70% already is shown by GC analysis. A DC analysis shows the corresponding hydroxylamine as intermediate product and does not allow any more educt to be recognized. The suspension is agitated at not higher than 45° C. overnight. Iodine starch paper shows by rapid testing the presence or absence of available oxygen. After the reaction is completed, excess oxidizing agent is reduced by saturated $Na_2SO_3$ solution and the reaction solution evaporated to dryness under vacuum. The residue is subsequently taken up in diethylether/5% NaOH, the phases separated and extracted two times more with diethylether. The combined organic phase is washed once with saturated $NaHCO_3$ solution and once with saturated NaCl solution, dried over $MgSO_4$ and concentrated by evaporation.

The NMR raw spectrum already shows a high purity of the raw product (GC %:98.7) in the case of the compound of general formula II with $R^1$=Me, which product is isolated with 146 g (93%) in colorless, crystalline form. It can be recrystallized out of diethylether. Melting point: 125° C.

B) Oxidation to the Compound of Formula II Using hydrogen peroxide and a Catalytic Amount of methyltrioxyrhenium, MTO (0.90 mmole) of the compound of type II of WO 97/10203 is placed in 20 mL EtOH (industrial) in a receiver and compounded under agitation with 0.35 g=0.31 mL 35% aq $H_2O_2$ (3.60 mmoles) and 9 mg (0.036 mmole=4 molar %) methyltrioxyrhenium at RT. The mixture is agitated overnight at RT. After the reaction is completed, saturated $Na_2SO_3$ solution is added for the reduction of excess oxidizing agent (starch iodine paper indicates completion). The MTO is absorptively removed by eluting over a silica-gel flash column. The mixture is rewashed twice with 15 mL EtOH each time. The eluate is evaporated to dryness under vacuum and taken up in diethylether/$H_2O$. The aqueous phase is extracted twice with 15 mL diethylether, the combined organic phase washed with saturated NaCl solution, dried over $NaSO_4$ and evaporated to dryness under vacuum.

In the case of II with R¹=Me a colorless, crystalline solid is obtained as raw product in 195 mg (92%).

C) Reaction of the Compound of Structural Type II to a Compound of Type IV Using the Example of the Preparation of (3S,5S,6S,9R)-3-tert-butyl-4-hydroxy-6-isopropyl-1,9-dimethyl-1,4-diazaspiro[4.5]decan-2-one 100 ml of a solution of 50.0 g (0.21 mole) II (R¹=Me) in 100 ml toluene, 340.6 g (1.26 moles) potassium peroxodisulfate in 1000 ml water and 157 g (1.26 moles) tert-butylhydrazine hydrochloride in 1000 ml 10% sodium hydroxide solution are placed into a 4 l multi-neck flask and vigorously agitated. Subsequently, another 100 ml of the three solutions are added simultaneously every 30 min during which the initial production of nitrogen is observed in each instance as reaction control. 30 min after the last addition the organic phase is separated off and the aqueous phase washed twice with approximately 300 ml toluene. The combined organic phases are washed twice again with water and dried with sodium sulfate. After removal of the solvent under vacuum, 53.4 g raw product colored with a slightly yellowish color is obtained (yield=85.8%), which is present in pure form according to NMR spectra.

43.4 g (0.147 mole) colorless crystals are obtained by recrystallization from cyclohexane (yield=69.9%).

Total yield after postcrystallization: 48 g (77.2%)

| R² | yield (%) | melting point (°C.) |
|---|---|---|
| $CH_2CH_3$ | 41 (60 conversion) | 176.7° C. |
| $C(CH_3)_3$ | 96 | 171.8 (decomposition) |
| $C_6H_5$ | 71 | * |

*¹H-NMR (400.1 MHz, CDCl₃): δ = 7.25–7.50 (m, 5 H, aromat. C—H̲); 4.84 (s, 1 H, NOH̲); 4.80 (s, 1 H, CH̲—C3); 2.85 (s, 3H NCH̲₃); 0.85–2.1 (m, 18 H, menthyl-CH̲ₓ) including 1.06 (d, 3H, CH̲₃—C11/13/14, ³J = 6.6 Hz); 0.99 (d, 3H, CH̲₃—C11/13/14, ³J = 6.6 Hz); 0.97 (d, 3H, CH̲₃—C11/13,14, ³J = 6.6 Hz).

D) Electrochemical Radical Alkylation of the Compound of General Formula II 1.0 g compound of type II (R¹=Me) (4.20 mmoles) is placed into 40 mL ethyl acetate (industrial) in a receiver and compounded with 500 mg tert-butylhydrazine hydrochloride (4.00 mmoles) as well as with 500 mg NaOH (12.50 mmoles) in 5 mL MeOH. The electrolysis is carried out in an undivided cell. A carbon rod anode (approximately 6 cm²) and a carbon rod cathode (approximately 6 cm²) are used as electrodes. A potential of min. 550 mV to a max. of 1000 mV vs. Ag/AgCl/KCl is put on the working electrode (anode). During the course of the electrolysis another 500 mg tert-butylhydrazine hydrochloride and 500 mg NaOH in 5 mL MeOH are added three times at 24 h intervals. After the reaction has been completed the precipitated NaCl is removed by suction. The organic phase is washed with H₂O and the solvent removed under vacuum. The matter is eluted over a silica-gel column with a 2:1 mixture of cyclohexane-:ethyl acetate. After evaporation to dryness under vacuum 1050 mg (87.5%) of a colorless, crystalline solid are obtained.

E) Preparation of (2S,5R,6S,9R)-3-tert-butyl-6-isoporopyl-4,9-dimethyl-1,4-diazasprio[4.5]decan-3-One hydrochloride 43.4 g (0.147 mole) of the compound of general formula IV (R¹=Me, R²=tBu, R³=OH) are dissolved in 200 ml ethanol and compounded with 200 ml 1.5 N HCl solution and 20 g Pd/C catalyst. The flask is briefly evacuated, gassed with hydrogen and the suspension agitated for 3 days. The catalyst is subsequently filtered off and washed intensively several times with 1 N HCl and ethanol. The collected filtrates are concentrated under vacuum and 49.4 g of a colorless, slightly moist raw product is obtained (yield=106%), which is present in pure form according to NMR spectra.

F) Release of L-tert-leucine methylamide hydrochloride

The 49.4 g of the product from (E) are suspended in 1200 ml 1 N HCl and 150 ml glacial acetic acid and heated up to 12 h under reflux. After removal of the solvent in a vacuum 25.6 g (0.142 mole) of a colorless solid is obtained (yield=96.5%) which is present in pure form according to NMR spectra. The ee value is 99.5%.

What is claimed is:

1. A method of producing enantiomer-enriched amino acids and amino-acid derivatives of formula (I) or acid addition salts thereof

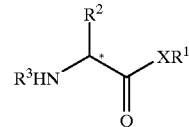

in which
  *=center of asymmetry
  X=O or NH
  R¹=H, $(C_1-C_6)$ alkyl, benzyl or $(C_3-C_6)$ alkoxycarbonylmethyl, and
  R²=H or $(C_1-C_6)$ alkyl, which can be interrupted or substituted with heteroatoms, which heteroatoms can be substituted themselves singly or multiply with $(C_1-C_3)$ alkyl, $(C_2-C_6)$ alkenyl, $(C_1-C_6)$ haloalkyl, halogen, aryl, which can be substituted singly or multiply with $(C_1-C_3)$ alkyl, hydroxy, halogen or $(C_1-C_3)$ alkoxy, aralkyl, which for its part can be substituted singly or multiply with $(C_1-C_3)$ alkyl, hydroxy, halogen or $(C_1-C_3)$ alkoxy, heteroaralkyl, and
  R³ signifies H, OH,
from diastereomer-enriched nitrons of the general formula (II)

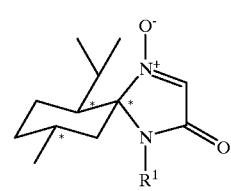

in which * and R¹ have the significance indicated above, wherein
  the nitron of the general formula (II) is reacted with a hydrazine derivative of the general formula (III)

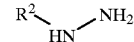

in which R² has the meaning indicated above
  in a solvent in the presence of a radical starter or under electrochemical conditions to obtain diastereomer-enriched compounds of the general formula (IV)

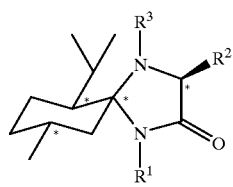

IV in which $R^1$ and $R^2$ have the meanings indicated above and $R^3$=OH, and the resulting product is subsequently hydrolyzed or first reduced to compounds of the general formula (IV), in which $R^1$ and $R^2$ have the meanings indicated above and $R^3$=H, and then hydrolyzed.

2. The method according to claim 1, wherein the radical substitution is carried out at temperatures between −78° C. and +150° C.

3. The method according to claim 1, wherein a two-phase system of toluene/water is used as solvent.

4. The method according to claim 2, wherein a two-phase system of toluene/water is used as solvent.

5. The method according to claim 1, wherein an oxidizing agent is used as radical starter.

6. The method according to claim 3, wherein an oxidizing agent is used as radical starter.

7. The method according to claim 1, wherein the reduction is carried out by means of catalytic hydrogenation by means of Pd/C.

8. The method according to claim 5, wherein the reduction is carried out by means of catalytic hydrogenation by means of Pd/C.

9. The method according to claim 1, wherein the hydrolysis is carried out in an acidified solvent.

10. The method according to claim 5, wherein the hydrolysis is carried out in an acidified solvent.

11. The method according to claim 1, wherein in the case of IV with $R^3$=H the hydrolysis is carried out in aqueous hydrochloric acid.

12. The method according to claim 10, wherein in the case of IV with $R^3$=H the hydrolysis is carried out in aqueous hydrochloric acid.

13. The method according to claim 1, wherein in the case of IV with $R^3$=OH the hydrolysis is carried out by means of hydrochloric acid in alcoholic solution.

14. The method according to claim 11, wherein in the case of IV with $R^3$=OH the hydrolysis is carried out by means of hydrochloric acid in alcoholic solution.

15. The method according to claim 1, wherein menthone produced after the hydrolysis is recycled.

16. The method according to claim 14, wherein menthone produced after the hydrolysis is recycled.

17. The method according to claim 1, wherein the oxidation to the compound of general formula (II) is carried out by means of magnesium monoperoxyphthalic acid (MMPP) or using methyltrioxorhenium (MeReO$_3$) in the presence of $H_2O_2$.

18. The method according to claim 15, wherein the oxidation to the compound of general formula (II) is carried out by means of magnesium monoperoxyphthalic acid (MMPP) or using methyltrioxorhenium (MeReO$_3$) in the presence of $H_2O_2$.

19. A method of producing enantiomer-enriched amino acids or acid addition salts of formula (I)

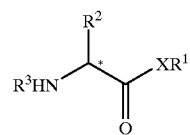

I in which
*=center of asymmetry
X=O or NH
$R^1$=H, ($C_1$–$C_6$) alkyl, benzyl or ($C_3$–$C_6$) alkoxycarbonylmethyl, and
$R^2$=H, ($C_1$–$C_6$) alkyl, which can be interrupted or substituted with heteroatoms, which heteroatoms can be substituted themselves singly or multiply with linear or branched ($C_1$–$C_3$) alkyl, ($C_2$–$C_6$) alkenyl, ($C_1$–$C_6$) haloalkyl, halogen, aryl, which can be substituted singly or multiply with ($C_1$–$C_3$) alkyl, hydroxy, halogen or ($C_1$–$C_3$) alkoxy, aralkyl which for its part can be substituted singly or multiply with (($C_1$–$C_3$) alkyl, hydroxy, halogen or ($C_1$–$C_3$) alkoxy, heteroaralkyl and
$R^3$ represents H or OH,
wherein compounds of the general formula (IV)

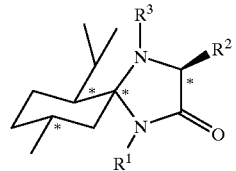

which were produced according to the method of claim 1 and in which $R^1$ and $R^2$ have the meanings indicated above and $R^3$=OH are eliminated to produce compounds of the general formula (V)

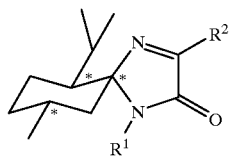

V in which $R^1$ and $R^2$ have the meanings indicated above, and are subsequently reduced and hydrolyzed.

20. The method according to claim 1 wherein said heteroatoms are selected from the group consisting of N, P, O, S and Si.

21. The method according to claim 1 wherein said aryl is naphthyl or phenyl.

22. The method according to claim 1 wherein said aralkyl is 2-naphthylmethyl, benzyl or, 1,1- or 1,2-phenethyl.

23. The method according to claim 1 wherein said heteroaralkyl is N-protected 3-indolylmethyl.

24. The method according to claim 5 wherein said oxidizing agent is selected from the group consisting of sodium peroxodisulfate, potassium peroxdisulfate, sodium percarbonate and sodium perborate.

25. The method according to claim 6 wherein said oxidizing agent is selected from the group consisting of sodium peroxodisulfate, potassium peroxodisulfate, sodium percarbonate and sodium perborate.

26. The method according to claim 19 wherein said heteroatoms are selected from the group consisting of N, P, O, S and Si.

27. The method according to claim 19 wherein said aryl is naphthyl or phenyl.

28. The method according to claim 19 wherein said aralkyl is 2-naphthylmethyl, benzyl or 1,1- or 1,2-phenethyl.

29. The method according to claim 19 wherein said heteroaralkyl is N-protected 3-indolylmethyl.

* * * * *